US009764125B2

(12) United States Patent
Ma

(10) Patent No.: US 9,764,125 B2
(45) Date of Patent: Sep. 19, 2017

(54) SEPTUM ACTUATOR WITH INSERTION DEPTH LIMITER AND COMPRESSION COMPENSATOR

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/073,428

(22) Filed: Mar. 17, 2016

(65) Prior Publication Data

US 2016/0199633 A1    Jul. 14, 2016

Related U.S. Application Data

(62) Division of application No. 13/766,543, filed on Feb. 13, 2013, now Pat. No. 9,320,881.

(51) Int. Cl.
*A61M 39/00* (2006.01)
*A61M 39/22* (2006.01)
*A61M 39/24* (2006.01)
A61M 39/26 (2006.01)

(52) U.S. Cl.
CPC .......... *A61M 39/221* (2013.01); *A61M 39/24* (2013.01); *A61M 2039/2426* (2013.01); *A61M 2039/2486* (2013.01); *A61M 2039/263* (2013.01); *Y10T 29/49826* (2015.01)

(58) Field of Classification Search
CPC .... A61M 39/04; A61M 39/26; A61M 39/045; A61M 5/158; A61M 5/24; A61M 5/284; A61M 5/286; A61M 5/2053

USPC ............ 604/86, 88, 148, 201, 244, 415, 87, 604/167.02, 202, 205, 288.02
See application file for complete search history.

(56) References Cited

U.S. PATENT DOCUMENTS

| 1,640,620 | A | | 8/1927 | Shaff | |
|---|---|---|---|---|---|
| 2,591,706 | A | * | 4/1952 | Lockhart | 604/90 |
| 3,192,949 | A | | 7/1965 | De See | |
| 3,831,629 | A | * | 8/1974 | Mackal et al. | 137/843 |
| 4,387,879 | A | * | 6/1983 | Tauschinski | 251/149.1 |
| 4,804,015 | A | * | 2/1989 | Albinsson | 137/614.03 |
| 4,838,855 | A | | 6/1989 | Lynn | |
| 5,269,771 | A | * | 12/1993 | Thomas | A61M 39/045 251/149.1 |
| 5,324,256 | A | * | 6/1994 | Lynn et al. | 604/540 |
| 5,509,912 | A | * | 4/1996 | Vaillancourt et al. | 604/537 |
| 5,520,665 | A | * | 5/1996 | Fleetwood | 604/537 |
| 5,555,908 | A | * | 9/1996 | Edwards et al. | 137/329.1 |
| 5,578,059 | A | * | 11/1996 | Patzer | 604/249 |

(Continued)

FOREIGN PATENT DOCUMENTS

EP          0 414 997 A1    3/1991

*Primary Examiner* — Scott Medway
(74) *Attorney, Agent, or Firm* — Jeanne Lukasavage; Craig Metcalf; Kirton McConkie

(57) ABSTRACT

A multi-use intravenous infusion assembly is presented which includes a septum actuator having various features to prevent over-insertion of the septum actuator through a slit in a blood control septum. By preventing over-insertion of the septum actuator, the slit of the septum is able to repeatedly self-close following removal of an external Luer device. Thus, the intravenous infusion assembly may be used repeatedly without exposing a clinician to blood and other infusion fluids.

8 Claims, 7 Drawing Sheets

(56) References Cited

U.S. PATENT DOCUMENTS

| | | | |
|---|---|---|---|
| 5,620,434 A * | 4/1997 | Brony | 604/406 |
| 5,674,206 A | 10/1997 | Allton et al. | |
| 5,814,024 A * | 9/1998 | Thompson et al. | 604/246 |
| 5,957,897 A * | 9/1999 | Jeffrey | 604/223 |
| 6,113,068 A * | 9/2000 | Ryan | 251/149.4 |
| 6,171,287 B1 | 1/2001 | Lynn et al. | |
| 6,183,448 B1 | 2/2001 | Mayer | |
| 6,595,981 B2 * | 7/2003 | Huet | 604/523 |
| 6,899,315 B2 * | 5/2005 | Maiville et al. | 251/149.4 |
| 6,932,795 B2 * | 8/2005 | Lopez et al. | 604/249 |
| 6,964,406 B2 | 11/2005 | Doyle | |
| 7,004,934 B2 * | 2/2006 | Vaillancourt | 604/533 |
| 7,008,404 B2 * | 3/2006 | Nakajima | 604/158 |
| 7,470,254 B2 * | 12/2008 | Basta et al. | 604/167.04 |
| 7,497,848 B2 | 3/2009 | Leinsing et al. | |
| 7,645,274 B2 * | 1/2010 | Whitley | 604/537 |
| 7,736,339 B2 * | 6/2010 | Woehr et al. | 604/164.08 |
| 7,815,614 B2 * | 10/2010 | Fangrow, Jr. | 604/256 |
| 7,837,658 B2 | 11/2010 | Cote et al. | |
| 8,002,765 B2 * | 8/2011 | Lopez | 604/533 |
| 8,066,670 B2 | 11/2011 | Cluff et al. | |
| 8,357,119 B2 * | 1/2013 | Stout et al. | 604/122 |
| 8,388,583 B2 | 3/2013 | Stout et al. | |
| 8,679,090 B2 * | 3/2014 | Anderson et al. | 604/533 |
| 9,320,881 B2 | 4/2016 | Ma | |
| 2001/0053895 A1 | 12/2001 | Vaillancourt | |
| 2002/0002351 A1 * | 1/2002 | Cote et al. | 604/247 |
| 2006/0118749 A1 | 6/2006 | Ryan et al. | |
| 2007/0233007 A1 * | 10/2007 | Adams | 604/168.01 |
| 2009/0281525 A1 * | 11/2009 | Harding et al. | 604/537 |
| 2010/0204648 A1 | 8/2010 | Stout et al. | |
| 2010/0204675 A1 * | 8/2010 | Woehr et al. | 604/500 |
| 2011/0319825 A1 | 12/2011 | Goral et al. | |
| 2012/0016266 A1 | 1/2012 | Burkholz | |
| 2013/0090610 A1 * | 4/2013 | Stout et al. | 604/256 |
| 2013/0165868 A1 | 6/2013 | Isaacson et al. | |
| 2014/0058336 A1 | 2/2014 | Burkholz et al. | |
| 2014/0296794 A1 | 10/2014 | Li | |

* cited by examiner

SEPTUM ACTUATOR WITH INSERTION DEPTH LIMITER AND COMPRESSION COMPENSATOR

RELATED APPLICATIONS

This application is a divisional of U.S. patent application Ser. No. 13/766,543, filed Feb. 13, 2013, titled SEPTUM ACTUATOR WITH INSERTION DEPTH LIMITER AND COMPRESSION COMPENSATOR, and is incorporated herein by reference.

BACKGROUND

Intravenous infusion systems are commonly used to access the vasculature of a patient as part of an infusion therapy procedure. An intravenous infusion system generally includes a fluid reservoir of IV bag that is connected to the patient via an intravenous catheter. The catheter is commonly coupled to a catheter adapter having a Luer-lock connector, or other connector-type for coupling the catheter adapter to a syringe, a section of intravenous tubing, or some other external Luer device. Fluid from the IV bag flow into the patient via the catheter adapter and the intravenous catheter.

In some instances, the catheter adapter further includes a blood control septum that is positioned within a fluid pathway running though the catheter adapter. The blood control septum is provided to allow selective flow of fluid through the fluid pathway. For example, the blood control septum may include a slit that may be bypassed when an external Luer device is coupled to the catheter adapter and directly engaging the septum. Upon removing the external Luer device, the slit is closed to prevent blood from leaking out of the catheter adapter.

In some instances, the catheter adapter further includes a septum actuator that is contacted by the external Luer device and advanced through the slit of the septum. The septum actuator is generally advanced through the septum to provide a permanent bypass or pathway through the septum. Thus, upon removal of the external Luer device, blood may freely flow out of the catheter adapter. Accordingly, many intravenous infusion systems which incorporate a septum actuator are intended for single use. For example, following catheterization of the patient, the septum is closed and blood is prevented from flowing out of the catheter adapter. However, once a clinician attaches an external Luer device to the catheter adapter, the septum actuator is advanced through the slit of the septum and fluid communication is established between the vasculature of the patient and the external Luer device. If the clinician wishes to remove the external Luer device, the clinician must either remove the entire intravenous infusion system from the patient, or must temporarily occlude the catheter in the patient's vein while the external Luer device is replaced with a new external Luer device or a cap. This limitation on some of the blood control catheter is due to the large variation of insertion depth in the existing external Luer devices. The distance the actuator is advanced depends on the insertion depth of the external Luer device. When the insertion depth is too low the actuator may not even open the septum slit to provide proper flow. At some minimum required insertion depth, the actuator will open up the septum slit just enough to provide adequate flow rate. If the external Luer device is removed at this insertion depth, the septum would push the actuator back out and close by itself. Further increase in insertion depth would not benefit the flow rate at all except pushing the actuator further into the septum slit. There exists a critical insertion depth beyond which the septum would not close by itself upon removal of the external Luer device. The difference between the critical insertion depth and the minimum required insertion depth is called the working distance of a self-sealing design and is dependent on the design of the septum, slit and the tip of the actuator. There is a very large variation in the insertion depth of the external Luer device, larger than the working distance of many blood control catheters. Such large variation in the insertion depth is largely due to the variation in the physical design of various Luer device and partly due to the variation in how tightly a Luer connection is made by clinician. In a typical catheter with blood control valve and septum actuator, the minimum required insertion depth is set to be equal or less than the minimum insertion depth of all existing external Luer device. However, when the insertion depth of the external Luer device is at the maximum of all existing external Luer device, the actuator will be pushed beyond the critical insertion depth making a reliable multi-use blood control catheter difficult to achieve.

Thus, while systems and methods currently exist to bypass a blood control septum as part of an infusion procedure, challenges still remain. Accordingly, it would be an improvement in the art to augment or replace current techniques with the system and methods discussed herein.

BRIEF SUMMARY OF THE INVENTION

The present invention has been developed in response to problems and needs in the art that have not yet been fully resolved by currently available systems and methods. Thus, these systems and methods are developed to provide a septum actuator having various features to prevent over-insertion of the septum actuator through the slit of the blood control septum. Thus, the systems and methods of the present invention provide an intravenous infusion assembly incorporating a septum actuator with insertion depth controls thereby ensuring that the blood control septum will consistently self-close following removal of an external Luer device from the assembly.

In some implementations, a septum actuator is provided having a body which includes a tip, a base, and a lumen extending therebetween. The septum actuator further includes a compression compensator which comprises a compressible and resilient material. The compression compensator is positioned between the base and the tip of the septum actuator. The compression compensator is compressed as the septum actuator is pushed through a slit of a blood control septum. A spring constant of the compression compensator is selected such that the compression of the compression compensator absorbs variations in the insertion depth of the tip through the slit in the septum due to variation in insertion depth of external Luer devices. Thus, the compression compensator achieves consistent insertion depths of the tip through the slit of the blood control septum.

The septum actuator may further include an insertion depth limiter to prevent over-insertion of the tip through a slit in a blood control septum. The insertion depth limiter generally comprises a physical feature on the outer surface of the septum actuator body, wherein the insertion depth limiter contacts a surface of the blood control septum, or another surface of the intravenous infusion assembly to arrest further movement of the tip through the slit. In this manner, over-insertion of the tip is prevented and the slit is able to self-close and push the tip out of the blood control septum.

In some instances, various features of the present invention provide an intravenous infusion assembly that prevents over-insertion of a septum actuator through a blood control septum of the assembly. Further, the septum actuator comprises various features to achieve consistent minimum and maximum insertion depths of the septum actuator tip through the slit of the blood control septum. Thus, various combinations of the features of the present invention provide an intravenous infusion system that may be used repeatedly to access the vasculature of a patient without exposing a clinician to blood and other infusion fluids.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL
VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE
INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
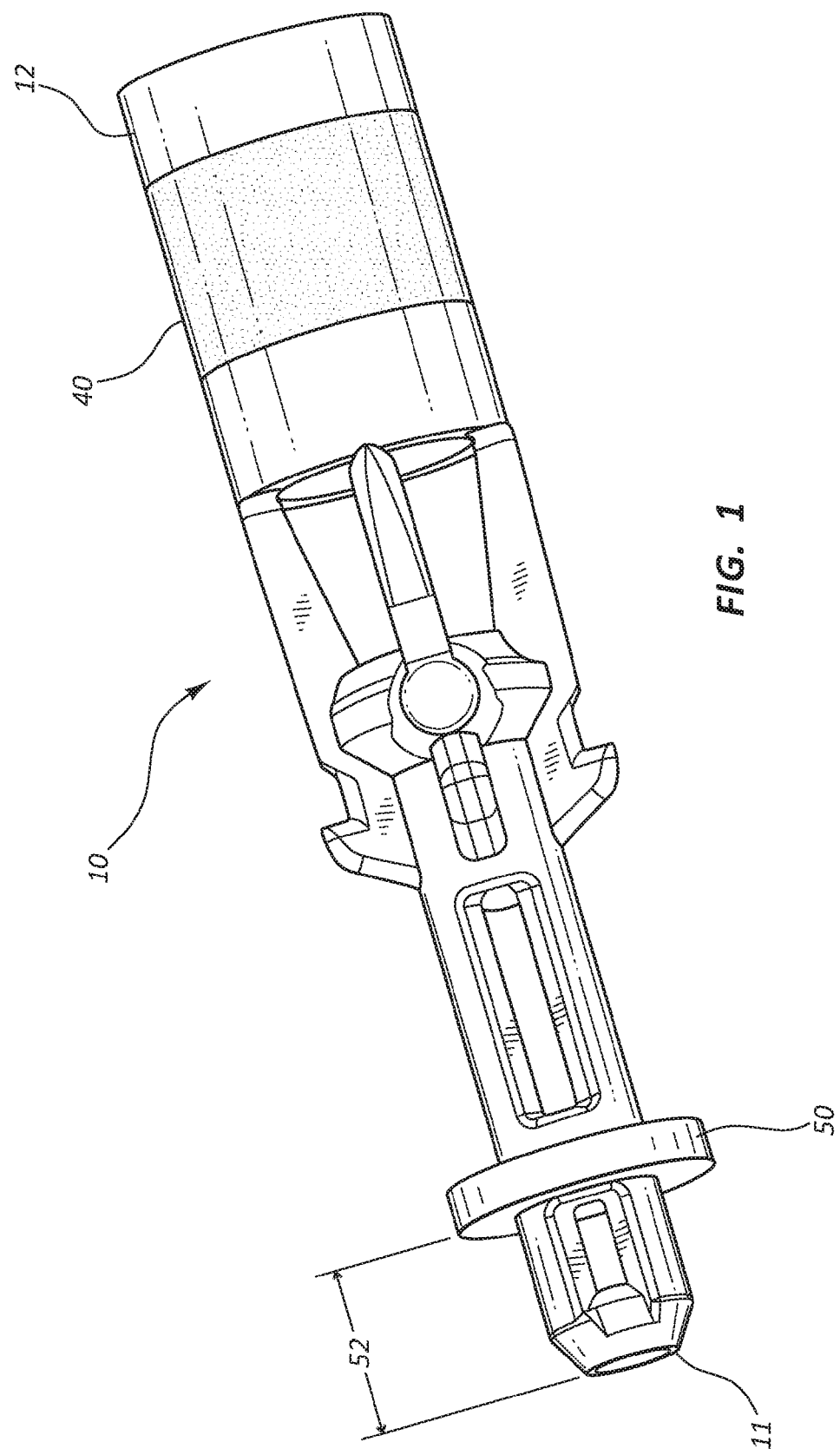
FIG. 1 is a perspective view of a septum actuator having an insertion depth limiter and a compression compensator in accordance with a representative embodiment of the present invention.

Referring now to FIG. 1, a septum actuator 10 is illustrated. Septum actuator 10 is commonly included as a component of an intravenous infusion assembly to assist in providing a pathway through a blood control septum. For example, in some instances an intravenous catheter (not shown) is coupled to a catheter adapter 20 having a fluid pathway 22 in which is positioned a blood control septum 30, as shown in FIGS. 2A through 5. In some instances, the blood control septum 30 divides fluid pathway 22 into a forward chamber 24 and a rearward chamber 26, thereby preventing uncontrolled flow of a fluid between forward and rearward chambers 24 and 26. This is commonly desired to prevent a clinician from being exposed to blood during a catheterization procedure. Upon accessing the patient's vasculature, blood flow through the catheter and into forward chamber 24. Without blood control septum 30, the blood would flow into rearward chamber 26 and out of the proximal opening 28 of catheter adapter 20. Accordingly, blood control septum 30 is provided as a means for controlling fluid flow through fluid pathway 22.

Septum actuator 10 may comprise various features to facilitate flow of fluid through blood control septum 30. For example, septum actuator 10 may comprise various vents and flow diverters to prevent stagnation of fluids flowing through fluid pathway 22. Septum actuator 10 may further include features for centering septum actuator 10 within fluid pathway 22. Further still, septum actuator 10 may comprise an antimicrobial coating to prevent growth and colonization of pathogens within fluid pathway 22.

In some embodiments, septum actuator 10 comprises a tip 11 having a chamfered surface to assist in biasing open a slit 32 of blood control septum 30. In some embodiments, the chamfered surface of tip 11 reduced the angular friction between tip 11 and slit 32 when tip 11 is inserted therein. Thus, when septum actuator 10 is released from being advanced through slit 32, slit 32 self-closes thereby pushing against the chamfered surface to move septum actuator 10 in a proximal direction 23 so that septum actuator 10 is again positioned in rearward chamber 26. The chamfered surface of tip 11 may be desirable to reduce the force needed to move septum actuator 10 when slit 32 self-closes.

Septum actuator 10 further includes a base 12 that is configured to be positioned near proximal opening 28 of catheter adapter 20. Base 12 generally comprises a rigid polymer material that is configured to be contacted by an external device that is inserted into proximal opening 28. When contacted by the external device, septum actuator 10 is advanced in a distal direction 21 through rearward chamber 26. As the external device is further inserted into proximal opening 28, tip 11 is forced through slit 32 of blood control septum 30 to provide a pathway therethrough.

In some embodiments, septum actuator 10 further comprises a compression compensator 40 that is positioned between tip 11 and base 12. Compression compensator 40 comprises a compressible material that is resilient following compression. For example, in some embodiments compression compensator 40 comprises a synthetic rubber material, a hydrogel, an elastomeric polymer, and other polymeric materials such as viscoelastic polymers and foam polyurethane. Compression compensator may include any density and compression properties in accordance with the uses and functions described herein.

In some instances, compression compensator 40 prevents over-insertion of tip 11 through slit 32 of blood control septum 30. For example, in some embodiments an external Luer device is inserted into proximal opening 28 to advance tip 11 through slit 32 of septum 30. The septum would resist the axial motion depending on the axial spring constant of the septum design. In some embodiments, the spring constant of the compression compensator is designed to be the same as the axial spring constant of the septum. In such cases, half of the insertion depth of the external Luer devices is absorbed through deformation of the compression compensator. The tip of the actuator only advances half of the distance of the insertion depth. Therefore the actuator effectively reduces the insertion depth variation of the existing external Luer device by 50%. At a minimum insertion depth, the compression compensator is slightly compressed and the blood control septum is just opened enough to have adequate flow rate. At maximum insertion depth the compression compensator is compressed about 50% of the insertion depth and the tip of the actuator is advanced less than the critical insertion depth. In both cases, the septum will push the actuator out upon the removal of the external Luer device.

In other embodiments, the spring constant of the compression compensator is designed to be 50% less than the axial spring constant of the septum. In such cases, two third of the insertion depth of the external Luer devices is absorbed through deformation of the compression compensator. The tip of the actuator only advances one third of the distance of the insertion depth. Therefore the actuator effectively reduces the insertion depth variation of the existing external Luer device by 67%. Ideally, the spring constant of the compression compensator is chosen such that the ratio of the working distance of the self-sealing design of the septum to the insertion depth variation of the existing external Luer device is greater than the ratio of the spring constant of the compression compensator to the sum of the spring constant of the compression compensator and the axial spring constant of the septum.

In some instances, the working distance of the self-sealing design of the septum is very small such that the target spring constant of the compression compensator is too low to be practical. Thus, in some embodiments septum actuator 10 further comprises an insertion depth limiter 50 that is coupled to the body of septum actuator 10 at a position between tip 11 and base 12. Insertion depth limiter 50 is provided to prevent over-insertion of tip 11 through slit 32.

Insertion depth limiter 50 generally comprises a rigid member that is fixedly coupled to septum actuator 10 at a determined distance 52 from tip 11. In some instances, insertion depth limiter comprises a molded surface of septum actuator 10. In other embodiments, insertion depth limiter 50 comprises a rigid ring member that is fitted onto the body of septum actuator and secured via a know method. For example, insertion depth limiter 50 may be secured to septum actuator via an adhesive, a plastic weld, or a friction fit.

Distance 52 is largely determined based upon the critical insertion depth of tip 11 through slit 32 of blood control septum 30. The critical insertion depth of tip 11 is understood as the maximum depth of tip 11 into slit 32 that still permits slit 32 to self-close and thereby push tip 11 out of slit 32. A minimum insertion depth of tip 11 is understood to be the minimum depth of tip 11 through slit 32 of septum 30 that permits fluid to flow through slit 32 at a desired flow rate. As with the critical insertion depth, the minimum insertion depth also permits slit 32 to self-close thereby pushing tip 11 out of slit 32. As slit 32 self-closes, septum actuator 10 is moved in a proximal direction 23. For example, upon removal of an external Luer device, septum actuator 10 is pushed in proximal direction 23 by the act of slit 32 self-closing. The result of slit 32 self-closing provides the configuration of blood control septum 30 and septum actuator 10, as shown in FIG. 2.

Figure 2A:
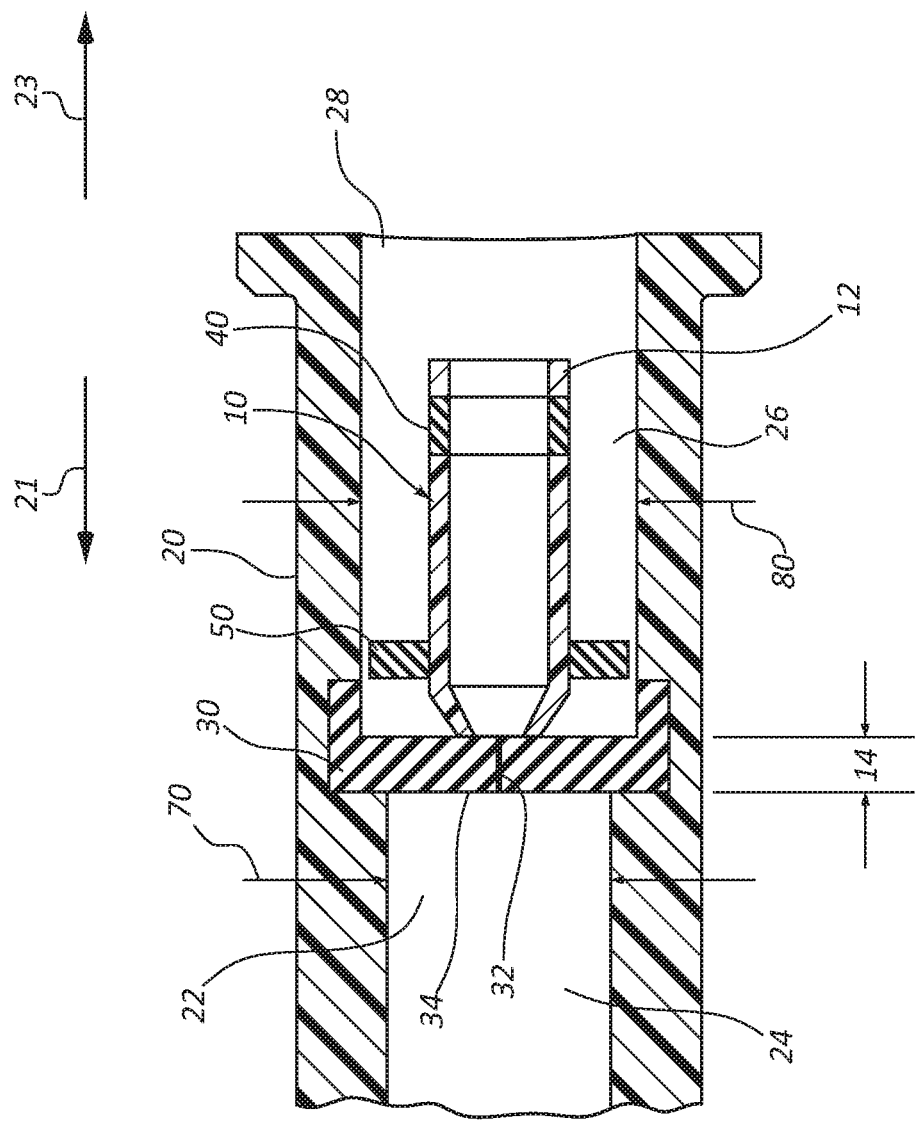
FIG. 2A is a cross-section, side view of a catheter assembly having a blood control septum and septum actuator in an inactivate configuration in accordance with a representative embodiment of the present invention.
Figure 2B:
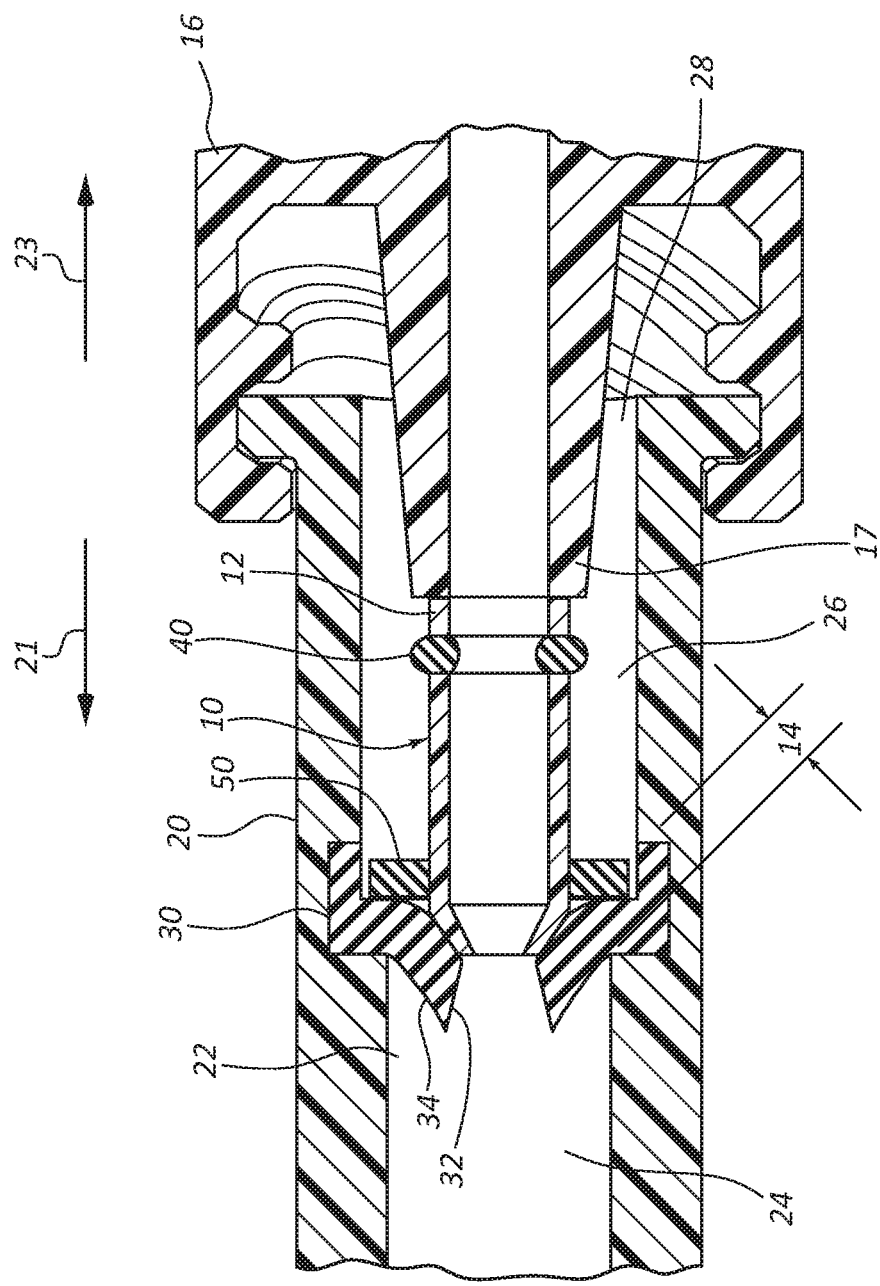
FIG. 2B is a cross-section, side view of a catheter assembly having a blood control septum and septum actuator in an activated configuration, wherein the compression compensator of the septum actuator is compressed in accordance with a representative embodiment of the present invention.

Referring now to FIGS. 2A and 2B, in some embodiments the critical insertion depth of tip 11 through slit 32 of blood control septum 30 is controlled via an insertion depth limiter 50. In some instances, insertion depth limiter 50 comprises an outer diameter 80 that is approximately equal to or smaller than the inner diameter of rearward chamber 26. In some embodiments, forward chamber 24 further comprises a reduced inner diameter 70, such that outer diameter 80 is greater than inner diameter 70. As such, inner diameter 70 provides a physical barrier that prevents or limits movement of septum actuator 10 in distal direction 21. The interaction between insertion depth limiter 50 and inner diameter 70 prevents over-insertion of septum actuator 10 through blood control septum 30, as shown in FIG. 2B. In some embodiments, septum 30 is pinched between insertion depth limiter 50 and inner diameter 70 as septum actuator 10 is advanced through septum 30 to a maximum insertion depth.

Figure 3A:
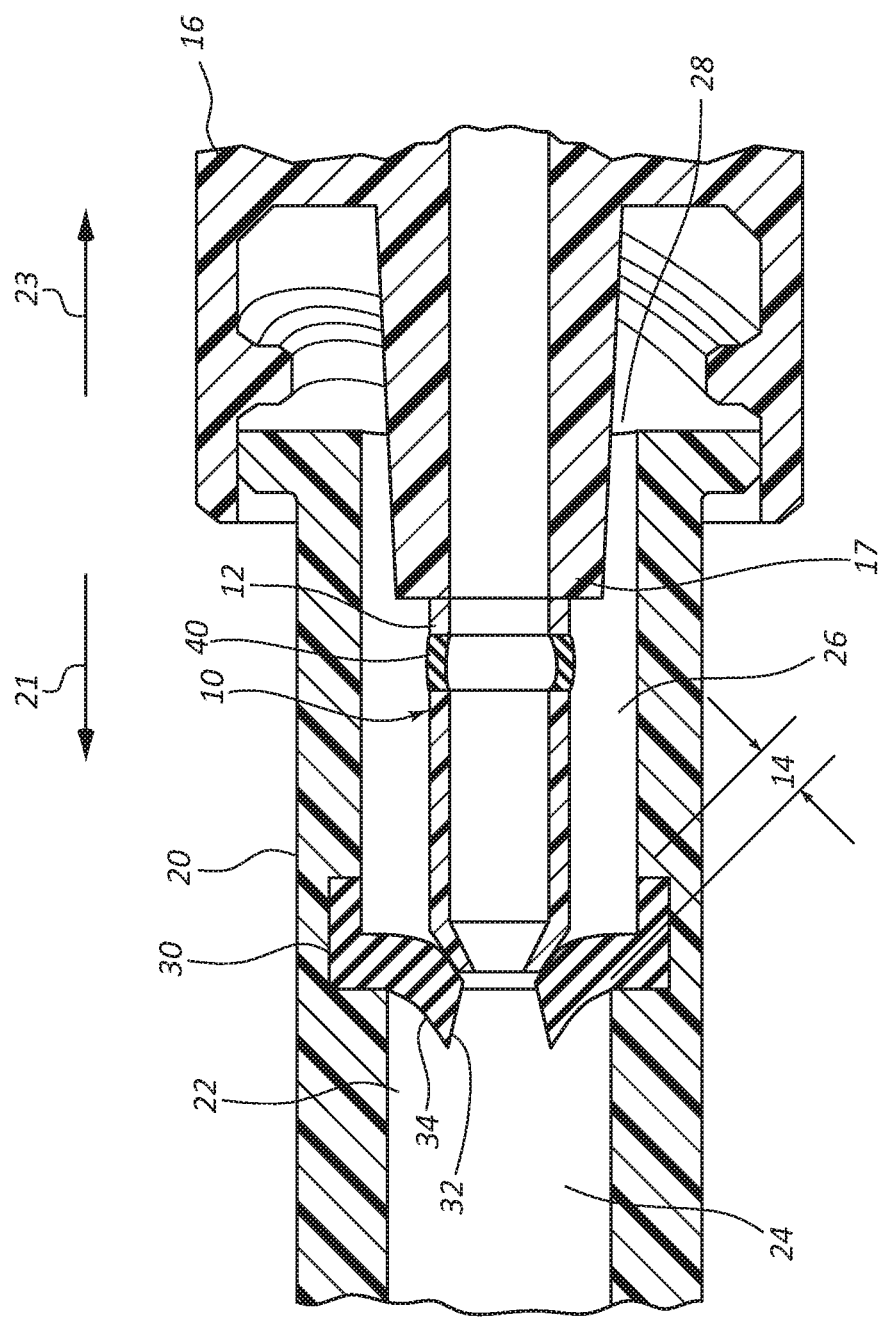
FIG. 3A is a cross-section, side view of a catheter assembly having a septum actuator inserted through a slit of a blood control septum at a minimum insertion depth, wherein the compression compensator of the septum actuator is slightly compressed in accordance with a representative embodiment of the present invention.

Upon insertion of external Luer device 16 into proximal opening 28, base 12 is contacted and septum actuator 10 advanced in distal direction 21. In some embodiments, compression compensator 40 is compressed as tip 11 contacts membrane 34 of septum 30. Tip 11 may also be inserted through slit 32 to a minimum required insertion depth, as shown in FIG. 3A. A minimum required insertion depth of tip 11 is understood as the minimum depth of tip 11 into slit 32 that permits a proper flow rate of fluid through slit 32. As with the critical insertion depth, the minimum required insertion depth permits slit 32 to self-close and thereby push tip 11 out of slit 32 upon removal of an external Luer device. In some instances, a minimum insertion depth is achieved as an external Luer device 16 with a short Luer is partially inserted into proximal opening 28 of catheter adapter 20. The short Luer and a not tightly made connection would compress the compression compensator 40 slightly, and the tip 11 is advanced through slit 32 to a minimum insertion depth, as shown.

Figure 3B:
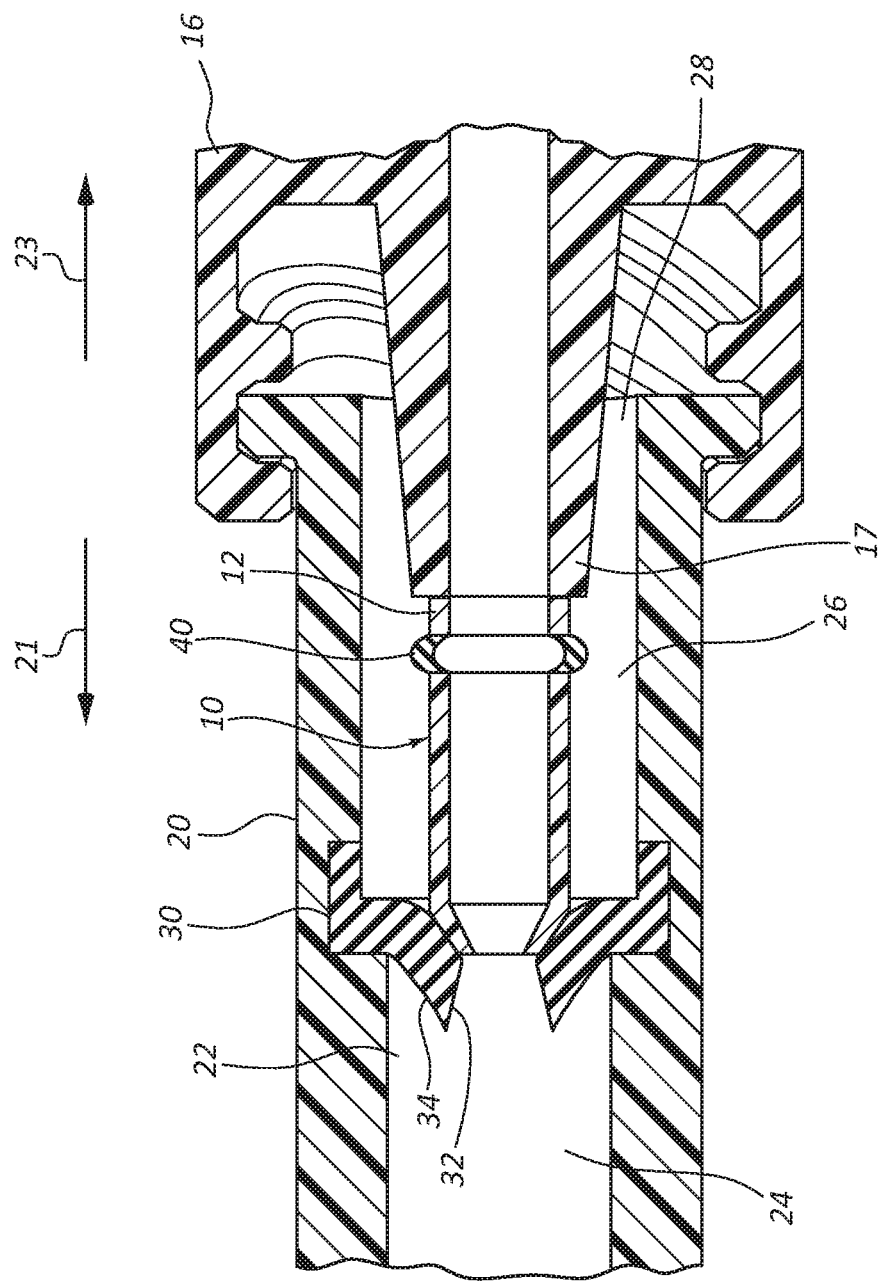
FIG. 3B is a cross-section, side view of a catheter assembly having a septum actuator inserted through a slit of a blood control septum at a maximum insertion depth wherein the compression compensator of the septum actuator is further compressed in accordance with a representative embodiment of the present invention.

Upon further insertion of external Luer device 16 into proximal opening 28 of catheter adapter 20, septum actuator 10 is further advanced through septum 30. In some instances, a critical insertion depth of septum actuator 10 through slit 32 is achieved when an external Luer device with a very long probe 17 is fully inserted into the proximal opening 28 of catheter adapter 20, as shown in FIG. 3B. The long probe 17 and a tightly made connection between catheter adapter 20 and external Luer device 16 maximally compresses compression compensator 40 and the tip 11 is advanced through slit 32 to a critical insertion depth, as shown. In some embodiments, over-insertion of external Luer device 16 into proximal opening 28 results in additional compression of compression compensator 40, rather than additional insertion of septum actuator 10 through blood control septum 30 through the use of an insertion depth limiter 50, as shown above.

Figure 4:
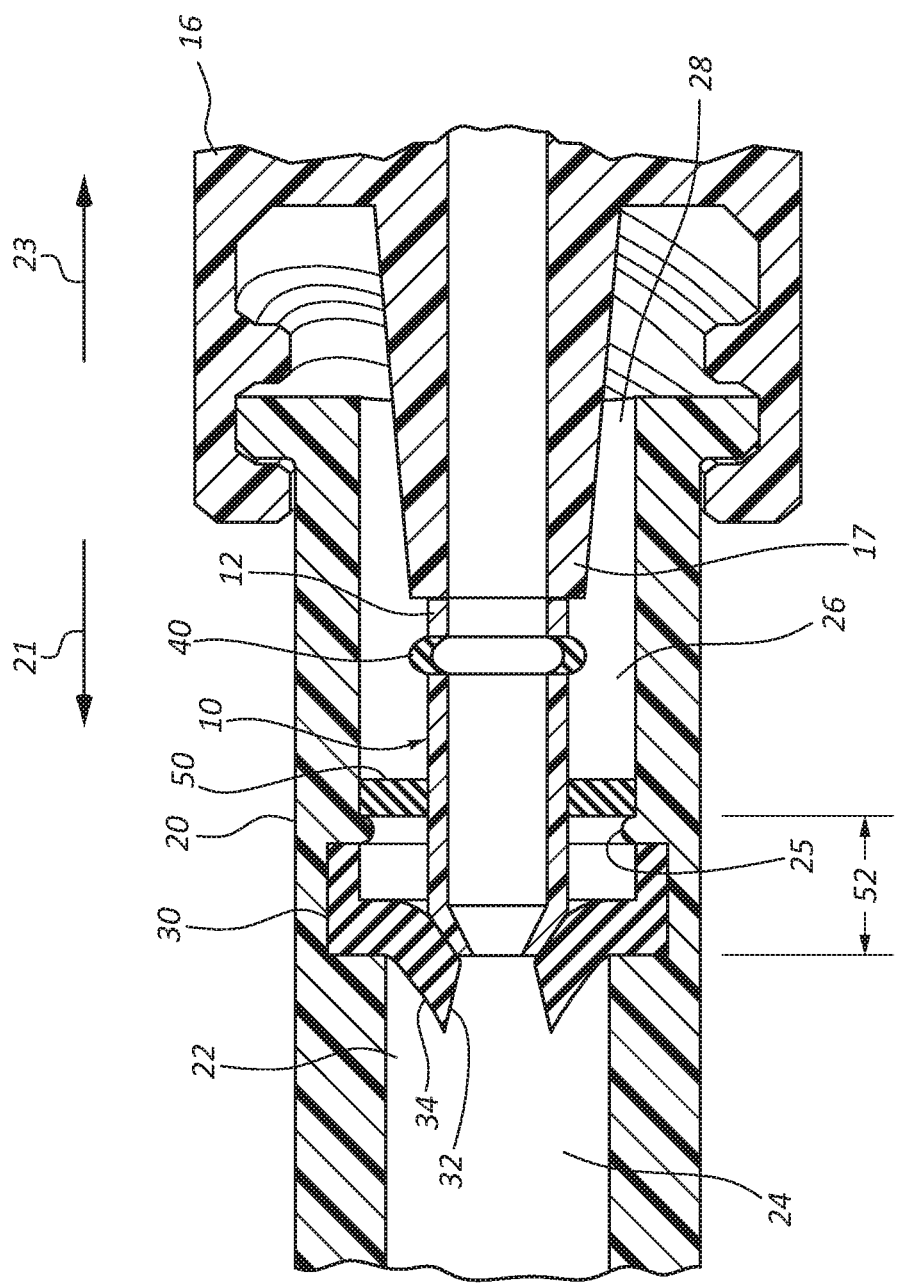
FIG. 4 is a cross-section, side view of a catheter assembly having a catheter adapter which includes a stop feature which limits the distal movement of the septum actuator tip through the slit of the blood control septum to a maximum insertion depth in accordance with a representative embodiment of the present invention.

Referring now to FIG. 4, in some embodiments septum actuator 10 an insertion depth limiter 50 that is configured to prevent over-insertion of septum actuator 10 through blood control septum 30. In some embodiments, an inner surface of catheter adapter 20 comprises a stop 25 that is configured to contact insertion depth limiter 50 to limit movement of septum actuator 10 in distal direction 21. In some instances, stop 25 is placed in proximal chamber 26 at a distance 52 from septum membrane 34. Thus, as tip 11 is advance through slit 32, insertion depth limiter 50 contacts the annular ridge 120 thereby limiting further movement of tip 11 in distal direction 21. Distance 52 may also comprise a critical insertion depth of tip 11, wherein the critical insertion depth comprises a depth of insertion for tip 11 whereby slit 32 is still capable of self-closing when external Luer device 16 is removed from proximal opening 28. Upon removal of external Luer device 16, septum actuator 10 is slid in proximal direction 23 as slit 32 self-closes.

Upon further insertion of external Luer device 16 into proximal opening 28, compression compensator 40 may be further compressed without resulting in additional insertion of tip 11 through slit 32. Alternatively, the spring constant of the compression compensator 40 may be larger than the axial spring constant of the septum. In such cases, the compression compensator will compressed less than the advancement of the tip of the actuator into the septum. When the spring constant of the compression compensator 40 is sufficiently larger than the axial spring constant of the septum, the compression compensator may not be compressed practically until an insertion depth limiter on the actuator has engaged with a stop feature. The compression compensator is only compressed upon further insertion of the external Luer device.

Stop 25 may comprise any feature of combinations of features to contact insertion depth limiter 50 and arrest distal movement of septum actuator 10. In some embodiments, stop 25 comprises an annular ring having an inner diameter that is less than an outer diameter of insertion depth limiter. As septum actuator 50 is advanced in distal direction 21, insertion depth limiter 50 contacts stop 25 to prevent over-insertion of tip 11 through slit 32. Thus, in some instances distance 52 comprises the distance at which critical insertion of tip 11 is achieved when insertion depth limiter 50 contacts stop 25.

Figure 5:
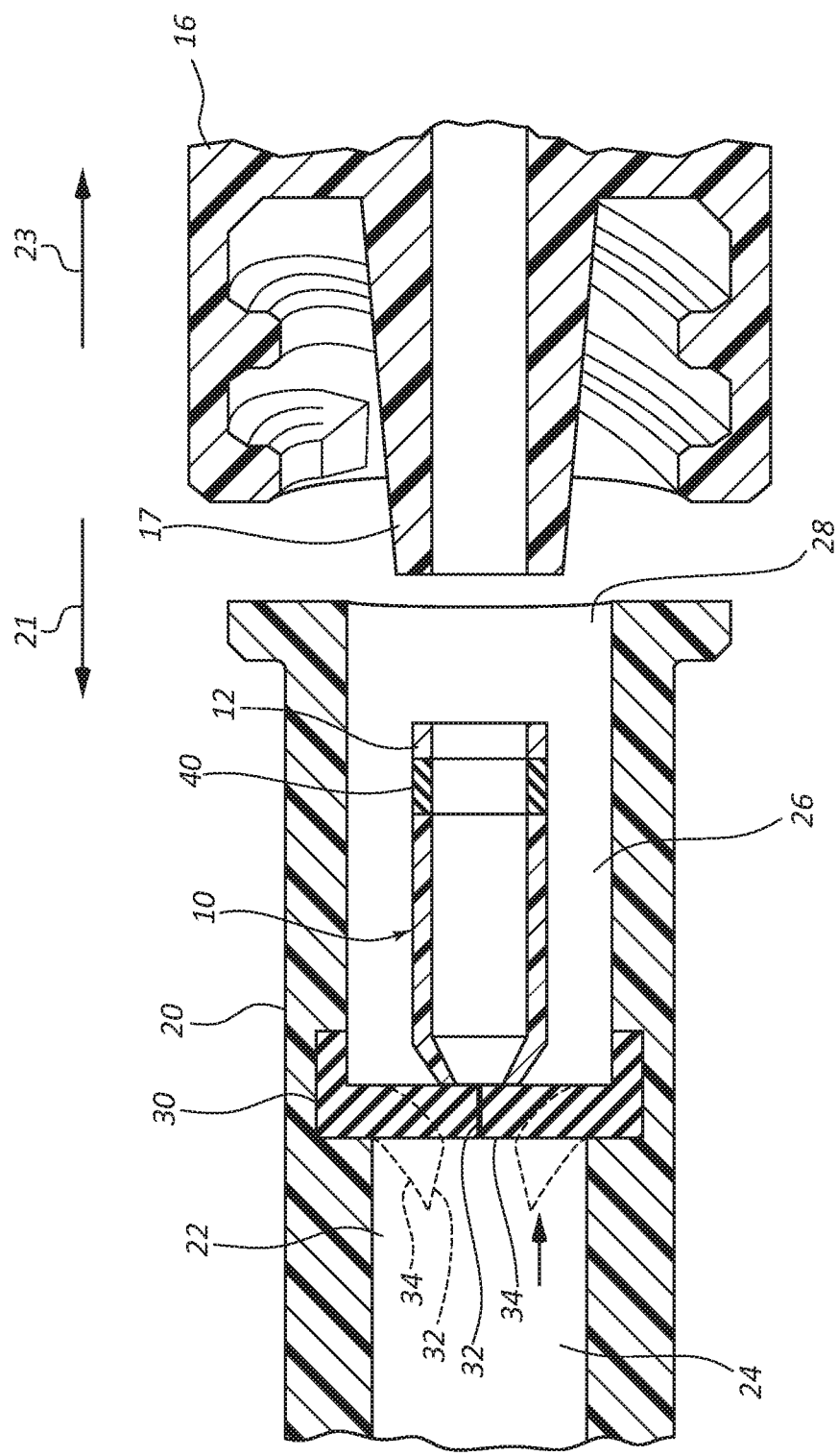
FIG. 5 is a cross-section, side view of a catheter assembly following removal of an external Luer device, wherein the slit has resumed its closed position thereby pushing the septum actuator out of the slit and the compression compensator resuming a relaxed configuration in accordance with a representative embodiment of the present invention.

Upon removal of external Luer device 16 from proximal opening 28, septum 30 undergoes self-closure thereby pushing tip 11 out of slit 32 and into rearward chamber 26, as shown in FIG. 5. In some embodiments, septum 30 comprises resilient polymer material have elastic properties. For example, in some embodiments septum 30 comprises silicon. In other embodiments, septum 30 comprises polytetrafluoroethylene. Further, upon removal of external Luer device 16, compression compensator 40 is released and resumes it uncompressed state and formation. The sealed configuration of slit 32 prevents leakage of fluids between forward and rearward chambers 24 and 26. The vasculature of the patient may be accessed again by reconnecting external Luer device 16, as discussed above.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
 a catheter adapter having a proximal end, a distal end, and a first lumen extending from the proximal end to the distal end;
 a septum positioned within the first lumen;
 a septum actuator slidably positioned within the first lumen proximal to the septum, the septum actuator configured to insert into a slit of the septum when separate devices are inserted into the proximal end of the catheter adapter, the septum actuator having a tip at a distal end, a base at a proximal end, and a compression compensator which is formed from a different material than the tip and the base, the compression compensator positioned between the tip and the base, the septum actuator including a second lumen that extends through the base, the compression compensator, and the tip, wherein the compression compensator defines a portion of the second lumen such that fluid flowing through the second lumen contacts an inner surface of the compression compensator;
 wherein, when the separate devices are inserted into the proximal end of the catheter adapter, the compression compensator compresses thereby compensating for variations in an insertion depth of the separate devices.

2. The catheter assembly of claim 1, wherein the septum actuator further includes an insertion depth limiter that contacts a surface of the septum or the catheter adapter to limit a depth of insertion of the septum actuator with respect to the septum.

3. The catheter assembly of claim 2, wherein the insertion depth limiter is positioned at a distance from the tip that prevents the tip from being inserted beyond a critical insertion depth.

4. The catheter assembly of claim 2, wherein the surface of the septum of the catheter adapter comprises a stop feature.

5. The catheter assembly of claim 1, wherein the tip is chamfered.

6. The catheter assembly of claim 1, wherein the compression compensator and the septum each have an axial spring constant that is substantially equal.

7. The catheter assembly of claim 1, wherein the compression compensator has an axial spring constant that is less than an axial spring constant of the septum.

8. The catheter assembly of claim 1, wherein the compression compensator has an axial spring constant that is approximately 50% less than an axial spring constant of the septum.

* * * * *